United States Patent [19]
Faulks et al.

[11] Patent Number: 5,776,122
[45] Date of Patent: Jul. 7, 1998

[54] ABSORBENT ARTICLE PROVIDING IMPROVED FECAL CONTAINMENT

[75] Inventors: Michael John Faulks, Neenah; Alan Francis Schleinz, Appleton, both of Wis.

[73] Assignee: Kimberly-Clark Worldwide, Inc., Neenah, Wis.

[21] Appl. No.: 362,611

[22] Filed: Dec. 21, 1994

[51] Int. Cl.$^6$ .................................................. A61F 13/15
[52] U.S. Cl. ........................................................ 604/385.2
[58] Field of Search ............................ 604/398, 385.1, 604/385.2

[56] References Cited

U.S. PATENT DOCUMENTS

| | | | |
|---|---|---|---|
| 4,388,075 | 6/1983 | Mesek et al. | 604/385 |
| 4,657,539 | 4/1987 | Hasse . | |
| 4,681,579 | 7/1987 | Toussant et al. | 604/385 R |
| 4,695,278 | 9/1987 | Lawson | 604/385.1 |
| 4,699,621 | 10/1987 | Stevens et al. | 604/385.1 |
| 4,699,823 | 10/1987 | Kellenberger et al. | 428/219 |
| 4,704,116 | 11/1987 | Enloe | 604/385.1 |
| 4,753,649 | 6/1988 | Pazdernik | 604/389 |
| 4,816,025 | 3/1989 | Foreman | 604/385.2 |
| 4,822,435 | 4/1989 | Igaue et al. | 156/164 |
| 4,822,668 | 4/1989 | Tanaka et al. . | |
| 4,846,823 | 7/1989 | Enloe | 604/385.2 |
| 4,900,384 | 2/1990 | Sanders et al. | 156/204 |
| 4,902,463 | 2/1990 | Tanaka et al. . | |
| 4,938,754 | 7/1990 | Mesek | 604/385.2 |
| 4,938,755 | 7/1990 | Foreman | 604/385.2 |
| 5,021,051 | 6/1991 | Hiuke | 604/385.2 |
| 5,030,303 | 7/1991 | Cucuzza | 156/604 |
| 5,032,120 | 7/1991 | Freeland et al. | 604/385.2 |
| 5,037,409 | 8/1991 | Chen et al. | 604/374 |
| 5,080,658 | 1/1992 | Igaue et al. | 604/385.2 |
| 5,147,343 | 9/1992 | Kellenberger | 604/368 |
| 5,167,653 | 12/1992 | Igaue et al. | 604/385.2 |
| 5,207,664 | 5/1993 | Blanco | 604/385.2 |
| 5,236,428 | 8/1993 | Zajaczkowski | 604/385.2 |
| 5,246,431 | 9/1993 | Minetola et al. | 604/385.2 |
| 5,331,015 | 7/1994 | DesMarais et al. | 521/62 |
| 5,366,453 | 11/1994 | Zehner et al. | 604/385.2 |
| 5,382,246 | 1/1995 | Kawano | 604/385.1 |
| 5,458,591 | 10/1995 | Roessler et al. | 604/364 |
| 5,476,457 | 12/1995 | Roessler et al. | 604/364 |

FOREIGN PATENT DOCUMENTS

| | | |
|---|---|---|
| 0 203 712 | 12/1986 | European Pat. Off. . |
| 0 219 326 | 4/1987 | European Pat. Off. . |
| 0 251 332 | 1/1988 | European Pat. Off. . |
| 0 274 752 | 7/1988 | European Pat. Off. . |
| 0 391 476 | 10/1990 | European Pat. Off. . |
| 2 554 325 | 5/1985 | France .......... A41B 13/02 |
| 2 256 803 | 12/1992 | United Kingdom . |
| 2280593 | 2/1995 | United Kingdom . |
| 2 281 501 | 3/1995 | United Kingdom . |

OTHER PUBLICATIONS

Great Britain Patents Act 1977: Search Report under Section 17, Great Britain Application No. GB 9526200.2 dated Jan. 27, 1997.

Primary Examiner—Michael J. Milano
Attorney, Agent, or Firm—Thomas M. Gage

[57] ABSTRACT

An absorbent article has a moisture barrier and an absorbent assembly disposed on the moisture barrier. In one embodiment, fecal containment members of the absorbent article are positioned transversely outward of the absorbent assembly between the absorbent assembly and each longitudinal side edge of the article. The fecal containment members have a wet compression recovery of at least about 85 percent and a mean pore size of at least about 1.5 millimeters.

32 Claims, 3 Drawing Sheets

ABSORBENT ARTICLE PROVIDING IMPROVED FECAL CONTAINMENT

BACKGROUND OF THE INVENTION

The present invention relates to articles for absorbing body fluids. More particularly, the invention pertains to an absorbent article providing improved containment of fecal matter.

Conventional disposable absorbent articles have typically included a liquid pervious bodyside liner, a liquid impervious backing sheet, and an absorbent material disposed between the bodyside liner and the backing sheet. To improve the fit of the absorbent article about the wearer, and to enhance the containment of waste materials, such products have also included elastic materials. Most commonly, these elastic materials have included threads, strands, or ribbons of elastic bonded to the backing sheet, either along the longitudinal sides or the longitudinal ends of the product.

Absorbent articles are called upon to contain both liquid waste and fecal matter. The fecal matter is often highly fluidic and expelled at high velocities. Although conventional fit and containment structures may function well to absorb and contain liquid waste, they do not necessarily function effectively with respect to fecal matter. Particularly, when the wearer is in a sitting position, the frequency of sideways leakage of highly fluidic, high velocity fecal matter past conventional containment structures is problematic.

Therefore, what is lacking and needed in the art is an absorbent article that is adapted to contain fecal matter, and in particular highly fluidic material that is expelled at high velocities.

SUMMARY OF THE INVENTION

In response to the discussed deficiencies in the prior art, a new absorbent article has been developed. The absorbent article provides enhanced protection against leakage of fecal matter.

In one aspect, the present invention concerns an absorbent article having longitudinal and transverse axes, longitudinal end edges, and longitudinal side edges extending between the longitudinal end edges. The absorbent article also includes a moisture barrier, an absorbent assembly disposed on the moisture barrier, and fecal containment members positioned transversely outward of the absorbent assembly between the absorbent assembly and each longitudinal side edge. The fecal containment members have a wet compression recovery of at least about 85 percent and a mean pore size of at least about 1.5 millimeters.

The fecal containment members function to interrupt lateral movement of fecal matter. The fecal containment members are formed of porous materials to provide sufficient void volume to collect highly fluidic fecal matter. Also, the fecal containment members desirably are dry resilient and wet resilient to maintain the void volume even after the diaper is insulted with urine and the wearer is in a sitting position.

In another aspect, the present invention concerns an absorbent article having longitudinal and transverse axes and including a moisture barrier, an absorbent assembly disposed on the moisture barrier, and a bodyside liner bonded to the moisture barrier and sandwiching the absorbent assembly therebetween. Containment flaps are disposed on the moisture barrier transversely outward of the absorbent assembly, with each containment flap having a base and a distal edge and defining therebetween a flap height. The base is spaced from the absorbent assembly by at least about 5 millimeters. Fecal passage members of the absorbent article each have an inner portion bonded to the bodyside liner, and an outer portion bonded to one of the containment flaps at an attachment point spaced from the base by from about 25 and about 95 percent of the flap height. As a result, fecal reservoirs are defined between the absorbent assembly, the containment flaps, the fecal passage members, and the moisture barrier.

This aspect provides a diaper with a pair of longitudinally extending fecal reservoirs. The reservoirs provide void spaces transversely outward of the absorbent assembly to contain fecal matter. The fecal passage members form part of the fecal reservoirs by maintaining portions of the containment flaps spaced from the absorbent assembly and bodyside liner. The fecal passage members are adapted to permit fecal matter to pass therethrough into the fecal reservoirs.

Numerous features and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use and not intended to be washed and reused.

(c) "disposed," "disposed on," "disposed with," "disposed at," "disposed near" and variations thereof are intended to mean that one element can be integral with another element, or that one element can be a separate structure bonded to or placed with or placed near another element.

(d) "elastic," "elasticized" and "elasticity" mean that property of a material by virtue of which it tends to recover its original size and shape after removal of a force causing a deformation.

(e) "elastomeric" refers to a material or composite which can be elongated by at least 25 percent of its relaxed length and which will recover, upon release of the applied force, at least 10percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

(f) "extension," "extend" and "extended" mean the change in length of a material due to stretching, expressed in units of length.

(g) "fabrics" is used to refer to all of the woven, knitted and nonwoven fibrous webs.

(h) "flexible" refers to materials which are compliant and which will readily conform to the general shape and contours of the wearer's body.

(i) "force" includes a physical influence exerted by one body on another which produces acceleration of bodies that are free to move and deformation of bodies that are not free to move. Force is expressed in grams per unit area.

(j) "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

(k) "inward" and "outward" refer to positions relative to the center of an absorbent garment, and particularly transversely and/or longitudinally closer to or away from the longitudinal and transverse center of the absorbent garment.

(l) "layer" when used in the singular can have the dual meaning of a single element or a plurality of elements.

(m) "liquid impermeable" when used to describe a layer or laminate means that liquid such as urine will not pass through the layer or laminate under ordinary use conditions in a direction generally perpendicular to the plane of the layer or laminate at the point of liquid contact.

(n) "member" when used in the singular can have the dual meaning of a single element or a plurality of elements.

(o) "nonwoven web" means a web of material which is formed without the aid of a textile weaving or knitting process.

(p) "operatively joined" and "operatively connected," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

(q) "stretch bonded" refers to an elastic member being bonded to the another member while the elastic member is extended at least about 25 percent of its relaxed length. Desirably, the term "stretch bonded" refers to the situation wherein the elastic member is extended at least about 100percent, and more desirably at least about 300percent, of its relaxed length when it is bonded to the other member.

(r) "stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

These terms may be defined with additional language in the remaining portion of the specification.

DETAILED DESCRIPTION OF THE PREFERRED EMBODIMENTS

Figure 1:
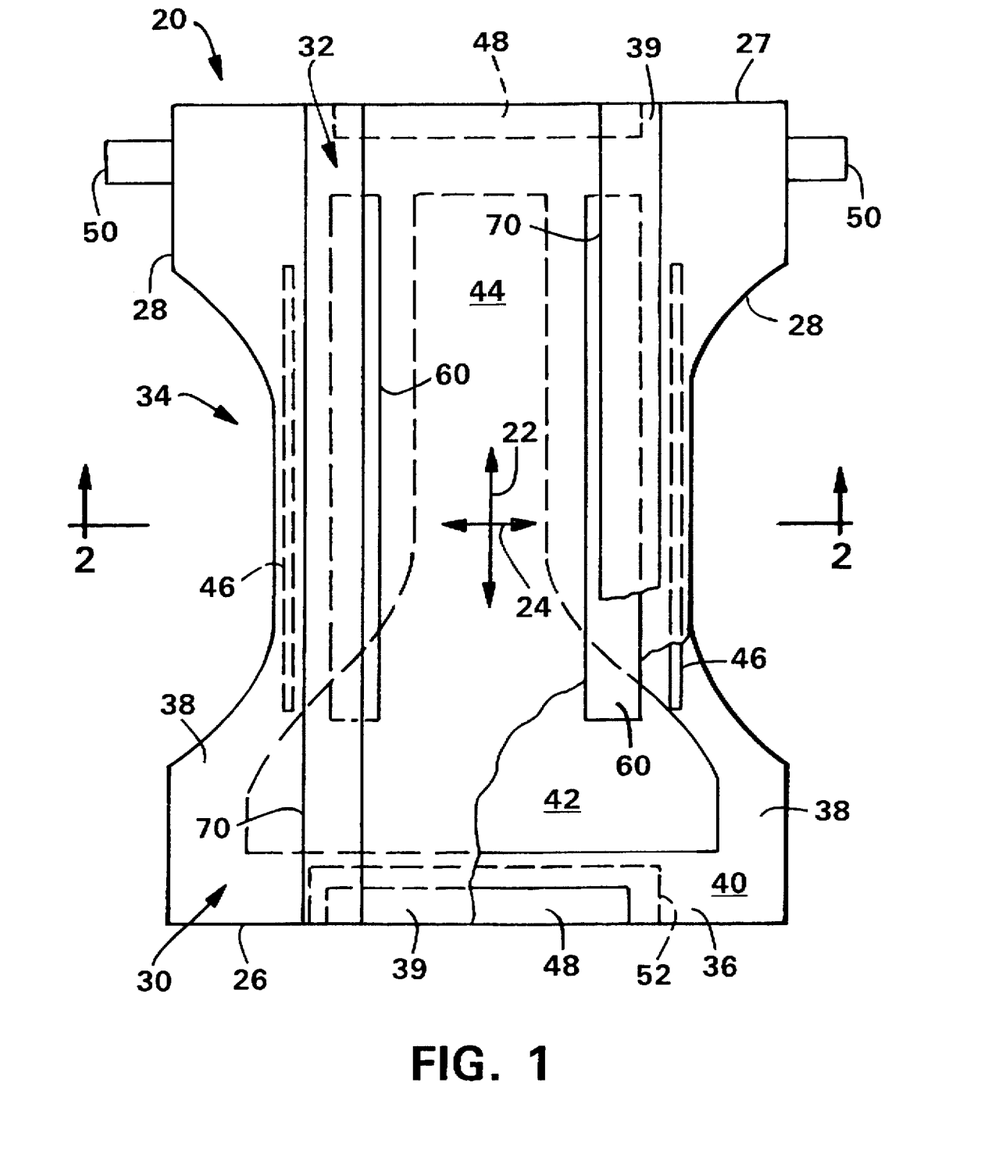
FIG. 1 representatively shows a top plan view of a disposable absorbent article according to the present invention, in a stretched and laid flat condition and with portions broken away for purposes of illustration.
Figure 2:
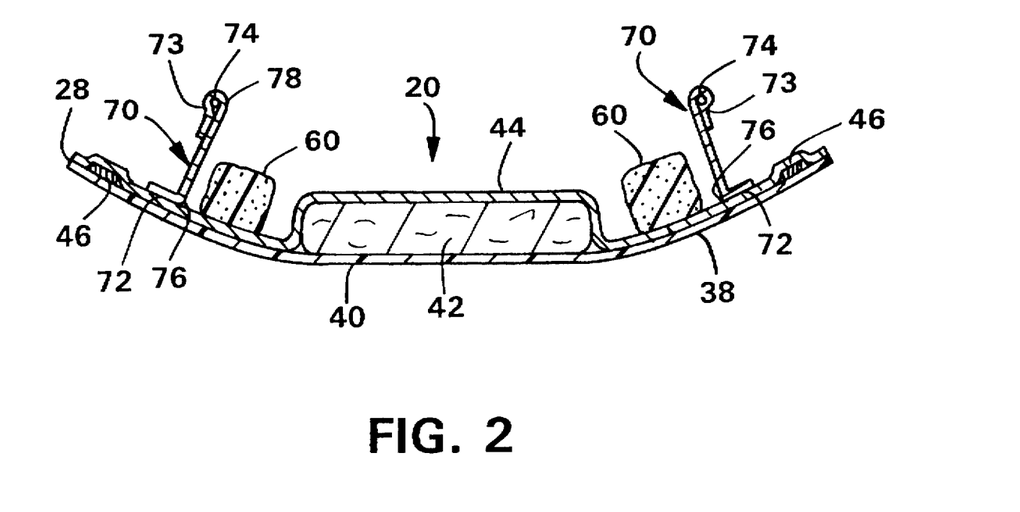
FIG. 2 representatively shows an enlarged transverse section view taken generally from the plane of the line 2—2 in FIG. 1, although in a relaxed condition rather than the stretched condition.

With reference to FIGS. 1 and 2, an absorbent article formed according to the present invention is shown for purposes of illustration as a disposable diaper 20. The invention may also be embodied in other types of absorbent articles such as adult incontinence garments, children's training pants, or the like. The diaper 20 includes fecal containment members 60 that are positioned and adapted to collect fecal matter, and thereby minimize the likelihood of leakage.

The illustrated diaper 20 defines longitudinal and transverse axes, represented by arrows 22 and 24 in FIG. 1. The diaper 20 has opposite, front and back longitudinal end edges 26 and 27, and longitudinal side edges 28 that extend between the longitudinal end edges. The diaper 20 includes a first or front waist region 30, a second or back waist region 32, and an intermediate, crotch region 34 positioned between and interconnecting the front and back waist regions. The outer edges of the diaper 20 define a periphery 36 in which the longitudinally extending side margins are designated 38 and the laterally extending end margins are designated 39. The side edges 28 define leg openings for the diaper 20, and optionally, are curvilinear and contoured. The end edges 26 and 27 are shown as generally straight, but optionally, may be curvilinear.

The front waist region 30 is contiguous with the front end edge 26 and extends longitudinally inward therefrom toward the transverse center line of the diaper 20. The back waist region 32 is contiguous with the back end edge 27 and extends longitudinally inward therefrom toward the transverse center line. The waist regions 30 and 32 comprise those upper portions of diaper 20 which, when worn, wholly or partially cover or encircle the waist or mid-lower torso of the wearer. The intermediate, crotch region 34 comprises that portion of diaper 20 which, when worn, is positioned between the legs of the wearer and covers the lower torso of the wearer. Thus, the crotch region 34 is the area where insults of urine and fecal matter typically occur in the diaper or other disposable absorbent article.

The diaper 20 includes a substantially liquid impermeable moisture barrier 40, an absorbent assembly 42 disposed on the moisture barrier, and a substantially liquid permeable bodyside liner 44 bonded to the moisture barrier to sandwich the absorbent assembly therebetween. The moisture barrier 40 and bodyside liner 44 are desirably longer and wider than the absorbent assembly 42 so that the peripheries of the moisture barrier and bodyside liner may be bonded together using ultrasonic bonds, thermal bonds, adhesives, or other suitable means. The peripheries of the moisture barrier 40 and the bodyside liner 44 typically form the side and end margins 38 and 39 of the diaper 20. The absorbent assembly 42 may be bonded directly to the moisture barrier 40 and/or the bodyside liner 44 using ultrasonic bonds, thermal bonds, adhesives, or other suitable means.

The moisture barrier 40 desirably comprises a material that is formed or treated to be liquid impermeable. Alternatively, the moisture barrier 40 may comprise a liquid permeable material and other suitable means (not shown), such as a liquid impermeable layer associated with the absorbent assembly 42, may be provided to impede liquid movement away from the absorbent assembly. The moisture barrier 40 may also be gas permeable, such that gases encountered during use of the absorbent garment are able to pass through the material under ordinary use conditions, over either all or part of its surface area.

The moisture barrier 40 may comprise a single layer of material or a laminate of two or more separate layers of material. Suitable moisture barrier materials include films, wovens, nonwovens, laminates of films, ovens, and/or nonwovens, or the like. For example, the moisture barrier 40 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 40 is a polyethylene film that has a nominal thickness of about 0.025 millimeter and a systematic matte embossed pattern, and that has been corona treated on both sides. Another suitable moisture barrier material is an adhesive or thermal laminate comprising a cast or blown film formed of polypropylene, polyethylene or the like, and a spunbond web formed of polypropylene fibers or polypropylene and polyethylene medium-crimped bicomponent fibers in a 50/50 side-by-side configuration.

The absorbent assembly 42 comprises materials adapted to absorb and retain liquid waste. The absorbent assembly 42 may comprise various absorbent materials, such as an air-formed batt of cellulosic fibers (i.e., wood pulp fluff) or a coform material composed of a mixture of cellulosic fibers and synthetic polymer fibers. The absorbent assembly 42 may also include compounds to increase its absorbency, such as 0–95 weight percent of organic or inorganic high-absorbency materials, which are typically capable of absorbing at least about 15 and desirably more than 25 times their weight in water. Suitable high-absorbency materials are described in U.S. Pat. No. 4,699,823 issued Oct. 13, 1987, to Kellenberger et al. and 5,147,343 issued Sep. 15, 1992, to Kellenberger, which are incorporated herein by reference. High-absorbency materials are available from various commercial vendors, such as Dow Chemical Company, Hoechst Celanese Corporation, and Allied Colloids, Inc. The absorbent assembly 42 may also include tissue layers or acquisition or distribution layers to help maintain the integrity of fibrous absorbents or transport liquids (not shown).

The bodyside liner 44 is formed of a liquid permeable material so that liquid waste, and possibly semi-solid waste as well, can pass through the liner and be absorbed by the absorbent assembly 42. Suitable bodyside liners 44 may comprise a nonwoven web or sheet of wet strength tissue paper, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 44 is desirably non-elastic and may be treated with a surfactant to aid in liquid transfer. In a particular embodiment of the invention, the liner 44 comprises a nonwoven, spunbond polypropylene fabric composed of about 2.8–3.2 denier fibers formed into a web having a basis weight of about 22 gsm and density of about 0.06 gm/cc. The fabric is surface treated with about 0.28 weight percent of a surfactant commercially available from Rohm and Haas Co. under the trade designation Triton X-102.

The diaper 20, which is in a stretched and laid flat condition in FIG. 1, is illustrated as having a periphery 36 that is hourglass or I shaped. Of course, the diaper 20 may optionally be T-shaped, rectangular, or irregularly-shaped. The general shape of the absorbent assembly 42 may correspond to the shape of the diaper 20 or assume a different shape such as the T-shape in FIG. 1. Desirably although not necessarily, the diaper 20 also includes elastic members in several locations to maintain the periphery 36 of the diaper 20 against the wearer and minimize the potential for leakage.

Elongated leg elastic members 46 are longitudinally oriented in each side margin 38, extending toward the front and back end edges 26 and 27. The leg elastic members 46 are positioned in the illustrated embodiment between the moisture barrier 40 and the bodyside liner 44. Using ultrasonic bonds, adhesives, thermal bonds, or other suitable means, the leg elastic members 46 are attached in a stretched condition to the moisture barrier 40, the bodyside liner 44, or both, in either a straight or a curved shape. The leg elastic members 46 can be arranged to draw and hold the side margins 38 of the diaper 20 against the legs of the wearer and form a seal therewith.

The diaper 20 may also include waist elastic members 48 (FIG. 1) in the end margins 39. The waist elastic members 48 are longitudinally oriented parallel to the transverse axis 24 of the diaper 20 to provide elasticized waists. Desirably, the waist elastic members 48 are positioned between the moisture barrier 40 and the bodyside liner 44 and secured in an extended condition to both the moisture barrier and the liner, using ultrasonic bonds, adhesives, thermal bonds or other suitable means.

The elastic members 46 and 48 may be formed of a dry-spun coalesced multifilament elastomeric thread sold under the tradename LYCRA and available from E. I. DuPont deNemours and Company. Alternately, the elastic members 46 and 48 may be formed of other typical elastics utilized in the diaper-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 40 and the liner 44. Other suitable elastic gathering means are disclosed in U.S. Pat. Nos. 4,938,754 to Mesek and 4,388,075 to Mesek et al.

Refastenable tape members 50 (FIG. 1) are operably connected to the side margins 38 in the back waist region 32 of the diaper 20. Each tape member 50 includes a fastening strip that may be releasably attached to an optional tape landing pad 52 located in the front waist region 30. The landing pad 52 is fixed by adhesive or other suitable means to the surface of the moisture barrier 40 that is remote from the absorbent assembly 42. The tape members 50 and the landing pad 52 are positioned so that the fastening strips may be attached to the landing pad when the diaper 20 is secured on a baby.

The tape members 50 and the landing pad 52 may be formed of a film comprising polypropylene, biaxially oriented polypropylene, polyester, or the like, and may be constructed in a manner as disclosed in U.S. Pat. No. 4,753,649 issued Jun. 28, 1988, to Pazdernik, which is incorporated herein by reference to the extent it is consistent herewith. Other suitable fastening devices, such as hooks, snaps, cohesive strips and the like, could be used in place of the tape members 50 and the landing pad 52.

In general, the moisture barrier 40, absorbent assembly 42, bodyside liner 44, elastic members 46 and 48, and fastening system components 50 and 52 of the diaper 20 may be assembled in a variety of well-known diaper configurations. Further, the diaper 20 may include other components in addition to those specifically illustrated. In particular, alternative diaper configurations which include additional features are disclosed in U.S. patent application Ser. No. 08/168,615 by T. Roessler et al., filed Dec. 16, 1993, and titled "Dynamic Fitting Diaper" (Attorney Docket No. 10,961); and U.S. patent application Ser. No. 08/168,615 by E. D. Johnson et al., filed Aug. 12, 1994, and titled "Diaper With Improved Lateral Elongation Characteristics" (Attorney Docket No. 11,629).

As referenced previously, the diaper 20 of FIGS. 1 and 2 also includes fecal containment members 60 which function to interrupt the lateral movement of high velocity fecal matter. Desirably formed of a porous resilient material, the fecal containment members 60 provide void volume to collect highly fluidic fecal matter. The fecal containment members 60 are desirably both dry resilient and wet resilient to maintain sufficient void volume even after the diaper 20 is insulted with urine, and even after the wearer is in a sitting position which tends to put pressure on the fecal containment members. The fecal containment members 60 may be bonded to the bodyside liner 44 using ultrasonic bonds, thermal bonds, adhesives, or other suitable means.

The illustrated fecal containment members 60 are in the shape of a generally straight bar but may alternatively be in the shape of a cylinder, strip, cube, or the like and be curved or partially curved. The shape of the fecal containment members 60 desirably provides a high void volume obstacle to sideways movement of fecal matter. Thus, the fecal containment members 60 desirably have a width dimension measured parallel to the transverse axis 24 of from about 5 to about 50 millimeters, and particularly from about 15 to about 25 millimeters for improved performance.

Further, the fecal containment members 60 desirably have a height dimension perpendicular to the plane containing the longitudinal and transverse axes 22 and 24 that is greater than the height dimension of the absorbent assembly 42. For example, the fecal containment members 60 may have a height dimension that is at least about 5 millimeters greater than the height dimension of the absorbent assembly 42. In particular embodiments, the width and height dimensions are selected so that the fecal containment members 60 have a cross sectional area measured parallel to the transverse axis 24 of at least about 2.5 square centimeters, and particularly from about 7.5 to about 12.5 square centimeters for improved performance.

The fecal containment members 60 desirably extend less than the entire distance between the front and back end edges 26 and 27 and are selectively positioned in the region where the absorbent assembly 42 is located. In the illustrated embodiment, the fecal containment members 60 are located in the crotch region 34 and in the back waist region 32 at least near the back end edge of the absorbent assembly 42. Alternatively, the fecal containment members 60 may extend the entire length dimension of the diaper 20 (not shown). In particular embodiments, the fecal containment members 60 have a length dimension of from about 24 to about 34 centimeters.

As shown in FIG. 1, the fecal containment members 60 may be positioned transversely outward of the absorbent assembly 42 in the crotch region 34 and on top of the absorbent assembly in the front waist region 30. Alternatively, the fecal containment members 60 may be positioned exclusively on top of the absorbent assembly 42 or exclusively transversely outward of the absorbent assembly (not shown). In any case, the fecal containment members 60 are desirably spaced from one another and located away from the longitudinal axis 22 so that fecal matter is likely to be expelled at a location which is between the members 60. In particular, the fecal containment members 60 are desirably spaced from one another by at least about 5 centimeters (cm), such as from about 5 to about 12 cm. The absorbent assembly 42 of the diaper 20 desirably has a width dimension in the crotch region 34 that is relatively narrow, such as from about 5 to about 9 cm.

Various materials can be used to construct the fecal containment members 60. For example, the fecal containment members 60 may be a nonwoven web of fibers, a foam, or any other suitable material which provides the desired function. The fecal containment members 60 may be a substantially hydrophobic material and, optionally, can be treated with a surfactant or otherwise to impart a desired level of wettability and hydrophilicity.

If the fecal containment members 60 comprise a foam material, any type of polymer which can be foamed and which can provide the desired function can be used. For example, the fecal containment members 60 may comprise an open-celled foam material made from polystyrene, polyvinylchloride, polyethylene, polyolefins, polyurethane, polyisocyanates, polyphenols, epoxy resins, silicon resins and the like. The foam material may also be rigid, semi-rigid or flexible. In a particular aspect of the invention, the fecal containment members 60 comprise a semi-rigid, polyurethane open-celled foam material.

Methods of forming such foam materials are well known to those skilled in the art. As is well known to those skilled in the art, the physical properties of the resultant foam materials can be varied broadly by controlling the ingredients and processing of the foam materials. Following the foaming of the polymer, the structure of the foam can also be modified by processes known to those skilled in the art to provide a greater number of open cells in the cell structure. For example, the percentage of open cells in the foam material can be increased to as great as 99 percent or higher. Foam materials having greater than 95 percent open cells are generally known as "reticulated" foams. Foam materials having an increased number of open cells are particularly desired for the fecal containment members 60 of the present invention. In a particular aspect of the invention, the fecal containment members 60 comprise a polyurethane foam material wherein at least 80 percent and desirably at least 95 percent of the cells present in the foam are open cells. For example, the fecal containment members 60 may comprise a polyurethane foam material designated Style #80.000 Federal Foam which is commercially available from Illbruck, Inc., a business having offices located in Minneapolis, Minn.

In a particular aspect of the invention, the fecal containment members 60 have a density (determined at a load of 0.2 psi) which is not more than about 0.050 grams per cubic centimeter and desirably from about 0.010 to about 0.030 grams per cubic centimeter to provide improved performance. Desirably, the fecal containment members 60 also have a basis weight of from about 100 to about 200 grams per square meter and more desirably from about 125 to about 175 grams per square meter. Moreover, the fecal containment members 60 are desirably substantially free of high-absorbency material such as absorbent gelling material such that the fecal containment members 60 do not retain high amounts of liquid.

The fecal containment members 60 may also be configured to have a mean pore size of at least about 1.5 millimeters and desirably from about 2.0 to about 4.0 millimeters. If the mean pore size is too small, fecal matter may not enter the void volume provided by the fecal containment members 60. The mean pore size can be determined according to any of various methods known to those skilled in the art. One such method is the Pore Size Test as set forth in the TEST PROCEDURES section below.

The fecal containment members 60 of the present invention function to hold the discharged fecal matter until the diaper 20 is removed. In one aspect of the present invention, it is particularly useful for the fecal containment members 60 to maintain a sufficient amount of void volume even when under load. For instance, the fecal matter should not be forced from the fecal containment members 60 when the wearer is in a position which causes pressure to be exerted on the containment members. Also, the fecal containment members 60 should continue to present an obstacle to lateral movement of fecal matter even when under load. The void volume of the fecal containment members 60 will vary as the load exerted upon it varies. As used herein, the term "void volume" refers to the void volume value as determined according to the void volume equation set forth in the Wet Compression Recovery Test in the TEST PROCEDURES section below.

In a particular aspect of the invention, the fecal containment members 60 have a void volume which is at least about 20 cubic centimeters per gram and desirably from about 30 to about 50 cubic centimeters per gram when under no compressive load. In addition, the diaper 20 can include sufficiently sized fecal containment members 60 to provide a void volume of at least about 3.0 cubic centimeters and desirably from about 5.0 to about 9.0 cubic centimeters under no load to provide improved performance. For example, the fecal containment members 60 may include about 0.2 grams of a polyurethane foam material having a void volume (under no load) of about 36 cubic centimeters per gram to provide about 7.2 cubic centimeters of void volume when under no load.

The fecal containment members 60 are also desirably both wet and dry resilient to preserve the void volume after exposure to urine and even after being compressed by the wearer. The resiliency of the fecal containment members 60 may be represented by the ability of the material to recover its original volume after being compressed. In a particular aspect, the fecal containment members 60 have a wet compression recovery of at least about 85 percent, desirably from about 90 to about 100 percent and more desirably from about 95 to about 100 percent. As used herein, the term "wet compression recovery" refers to the compression recovery value determined according to the Wet Compression Recovery Test as set forth in the TEST PROCEDURES section below. It is also desirable that the fecal containment members 60 maintain at least about 25 percent, desirably from about 30 to about 100 percent, and even more desirably from about 50 to about 100percent of their void volume (under no load) when under a load of 0.673 Newtons per square centimeter (0.975 pounds per square inch).

To enhance the containment and absorption of urine and facilitate containment of fecal matter, the diaper 20 of FIGS. 1 and 2 can optionally include a pair of containment flaps 70. The flaps 70, which extend longitudinally between the front and back end edges 26 and 27 of the diaper 20, are disposed on the moisture barrier 40 and positioned transversely inward of the side edges 28 and the leg elastic members 46. The fecal containment members 60 are desirably positioned immediately transversely inward of the containment flaps 70. Configurations of containment flaps 70 suitable for use on the illustrated diaper 20 are disclosed in U.S. Pat. Nos. 4,704,116 and 4,846,823 to Enloe, and U.S. patent application Ser. No. 208,816 of R. Everett et al., filed Mar. 4, 1994 and entitled "ABSORBENT ARTICLE HAVING AN IMPROVED SURGE MANAGEMENT" (Attorney docket No. 11,375), the disclosures of which are hereby incorporated by reference in a manner that is consistent herewith.

With specific reference to FIG. 2, the containment flaps 70 may be formed as a folded, elongated strip of material. The containment flaps 70 may, for example, comprise an attachment portion 72 along one longitudinal edge and a folded portion 73 along the opposite longitudinal edge. Elastic members 74 may be operatively joined to the containment flaps 70 within the folded portions 73, thereby causing the flaps to stand up from the bodyside liner 44 when the diaper 20 is worn. The particular number of elastic members 74 per containment flap 70 and the type of elastic material may vary. Suitable materials include a thin ribbon of elastic material or several strands of elastic string. Each elastic member 74, for instance, can be a dry-spun, coalesced multifilament elastomeric thread sold under the tradename LYCRA and available from E. I. DuPont deNemours and Company.

The attachment portion 72 of each containment flap 70 can be attached to the bodyside liner 44 using a continuous ultrasonic bond, a continuous strip of adhesive, a series of spot bonds, or other suitable means. Alternatively, the containment flaps 70 could be formed in portions of the bodyside liner (not shown). The longitudinal ends of each containment flap 70 are desirably laid flat on the bodyside liner 44 toward the longitudinal axis 22 and bonded to the bodyside liner. The region of the attachment portion 72 nearest the medial part of the containment flap 70 that is not bonded to the bodyside liner 44 is designated the base 76 of the flap. Oppositely, the part of the containment flap 70 that extends furthest from the bodyside liner 44 when the diaper 20 is worn is designated the distal edge 78 of the flap. The distance between the base 76 and the distal edge 78 defines a flap height of the containment flap 70, which is desirably greater than the height dimension of the fecal containment members 60, such as at least about 5 millimeters (mm) greater than the height dimension of the fecal containment members.

In use, the diaper 20 is positioned on the wearer and secured in place with the tape members 50. The fecal containment members 60 function to prevent leakage of fecal matter initially by providing an obstacle to lateral movement of fecal matter and then by providing a containment mechanism for the fecal matter. The large pore size of the containment members 60 make them well adapted to accept high velocity, highly fluidic fecal matter. Additionally, the resiliency of the containment members 60 allows them to remain effective under load. The containment flaps 70, when employed, provide further assistance in limiting lateral movement of fecal matter.

Figure 3:
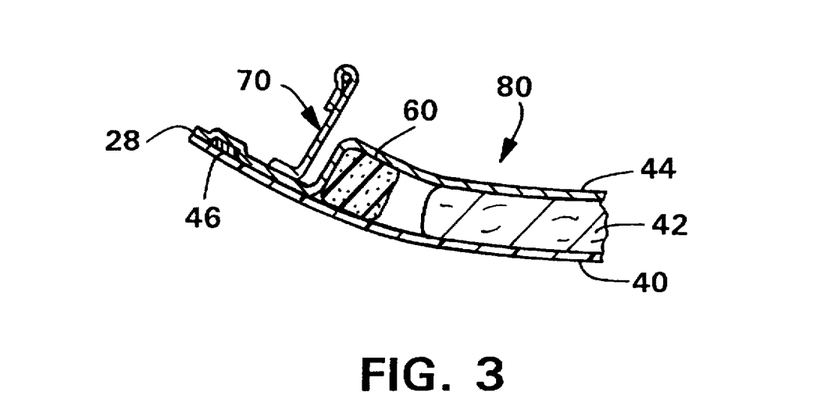
FIG. 3 representatively shows an enlarged transverse section view illustrating portions of an alternative absorbent article according to the present invention, in a relaxed condition.

An alternative embodiment of the invention is illustrated by a diaper 80 shown in a partial transverse section view in FIG. 3. Components similar to those previously described have been given the same reference numeral. In this embodiment, the bodyside liner 44 is positioned over the fecal containment members 60 so that the fecal containment members are disposed between the bodyside liner and the moisture barrier 40. At least in the crotch region 34 of the diaper 20, the fecal containment members 60 are desirably positioned transversely inward of the containment flaps 70.

The bodyside liner 44 of this embodiment is desirably formed or treated to permit passage of highly fluidic fecal matter therethrough. In particular, the bodyside liner 44 may be formed with a relatively open pore structure, or may be treated, such as by pin aperturing, slit and transverse-stretching, needle punching, or other suitable means, to permit passage of fluidic fecal matter. The treatment may encompass the entire bodyside liner 44 or only specific portions of the bodyside liner, such as those portions disposed on and near the fecal containment members 60.

Figure 4:
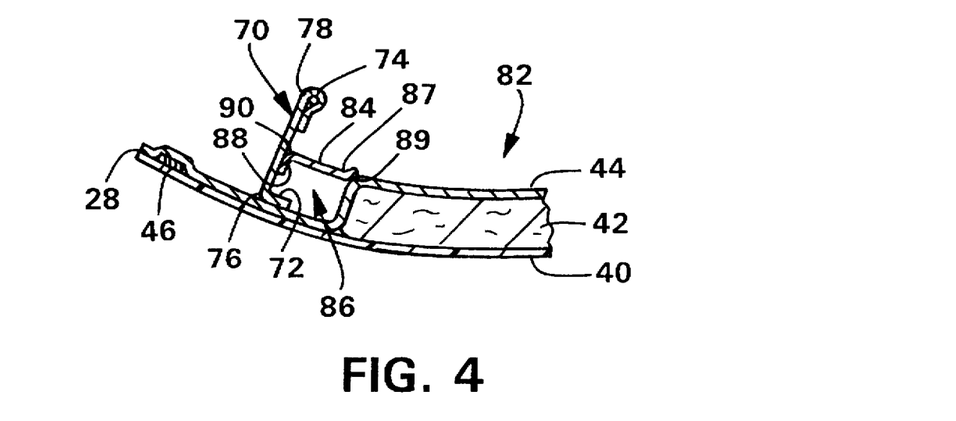
FIG. 4 representatively shows an enlarged transverse section view illustrating portions of another alternative absorbent article according to the present invention, in a relaxed condition.

A further alternative embodiment is illustrated by a diaper 82 shown in a partial transverse section view in FIG. 4. The diaper 82 includes a pair of fecal passage members 84, which are each bonded to the bodyside liner 44 and the adjacent containment flap 70, to form a pair of longitudinally extending fecal reservoirs 86. The fecal reservoirs 86 provide void spaces transversely outward of the absorbent assembly 42 to contain fecal matter. While only one fecal passage member 84 and one reservoir 86 are illustrated in FIG. 4, it can be appreciated that the opposite side of the diaper 82 is constructed in a similar manner to provide the second of the two fecal reservoirs.

The fecal passage members 84 function to form part of the fecal reservoirs 86, in part by maintaining portions of the containment flaps 70 spaced from the absorbent assembly 42 and bodyside liner 44. Each fecal reservoir 86 is formed with the absorbent assembly 42 and one of the containment flaps 70 functioning as sidewalls of the reservoir, the moisture barrier 40 functioning as the floor of the reservoir, and one of the fecal passage members 84 functioning as the ceiling of the reservoir. It should be recognized of course that in this embodiment portions of the bodyside liner 44 reside within the reservoir 86.

The fecal passage members 84 may be formed of the same material as the fecal containment members 60 described in relation to FIGS. 1–3. The fecal passage members 84 may, for instance, comprise a nonwoven web of fibers, a foam, or any other suitable material which is generally resilient and allows the passage of fecal matter therethrough. The fecal passage members 84 may be a substantially hydrophobic material and, optionally, can be treated with a surfactant or otherwise to impart a desired level of wettability and hydrophilicity. In one embodiment, the fecal passage members 84 comprise a semi-rigid, polyurethane foam material wherein at least 80percent and desirably at least 95 percent of the cells present in the foam are open cells. The fecal passage members 84 in such embodiment may have a width of about 1.5 cm. a thickness (determined at a load of 0.2 psi) of about 0.5 cm. and a length of about 10 cm.

The fecal passage members 84 are suitably configured to have a mean pore size which allows fecal matter to pass easily therethrough. The pore size in particular is desirably at least about 1.5 millimeters and desirably from about 2.0 to about 4.0 millimeters. Further, the fecal passage members 84 are desirably both wet and dry resilient, and in particular having a wet compression recovery of at least about 85 percent, desirably from about 90 to about 100 percent and more desirably from about 95 to about 100 percent. As used herein, the term "wet compression recovery" refers to the compression recovery value determined according to the Wet Compression Recovery Test as set forth in the TEST PROCEDURES section below. Moreover, the fecal passage members 84 are desirably substantially free of high-absorbency material so that they do not retain high amounts of liquid.

The fecal passage members 84 each have an inner portion 87 bonded to the bodyside liner 44 and an outer portion 88 bonded to one of the containment flaps 70. The inner portion 87 is desirably bonded to the bodyside liner 44 at a first attachment point 89 that is located on top of the bodyside surface of the absorbent assembly 42 or along a side edge of the absorbent assembly, as in FIG. 4, so that the region between the inner portion 87 and the moisture barrier 40 forms a sidewall of the fecal reservoir 86. Similarly, the outer portion 88 is desirably bonded to the containment flap 70 at a second attachment point 90 that is located between the base 76 and the distal edge 78. In particular, the outer portion 88 is suitably bonded to the containment flap 70 at an attachment point 90 that is spaced from the base 76 by from about 25 to about 95 percent of the flap height, and more particularly by from about 50 to about 75 percent of the flap height. As a result, the region of the containment flap 70 between the outer portion 88 and the moisture barrier 40 forms another sidewall of the fecal reservoir 86. Also, the outer portion 88 is desirably attached to the containment flap 70 so that the elastic member 74 of the containment flap is positioned between the second attachment point 90 and the distal edge 78.

The size of the fecal reservoirs 86 is a function in part of where the containment flap 70 is directly (not shown) or indirectly (FIG. 4) bonded to the moisture barrier 40. Specifically, the size of the reservoirs 86 is determined in part by the spacing of the base 76 of each containment flap 70 from the side edge of the absorbent assembly 42. Desirably, the base 76 of each containment flap 70 is spaced from the absorbent assembly 42 by at least about 5 millimeters (mm), and more particularly by at least about 8 mm. such as from about 10 to about 50 mm for improved performance.

Figure 5:
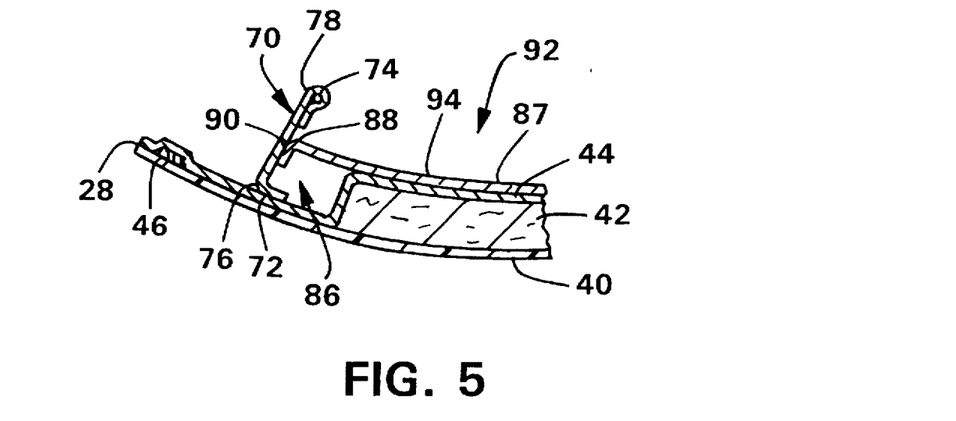
FIG. 5 representatively shows an enlarged transverse section view illustrating portions of a further alternative absorbent article according to the present invention, in a relaxed condition.

Another embodiment of the invention is shown as diaper 92 in the partial transverse section view of FIG. 5. The diaper 92 includes a fecal passage layer 94 which is disposed on the absorbent assembly 42. The fecal passage layer 94 has an inner portion 87 positioned over the absorbent assembly 42 and outer portions 88 located on either side of the inner portion.

Each outer portion 88, only one of which is shown in FIG. 5, is bonded to one of the containment flaps 70 at an attachment point 90 that is located between the base 76 and the distal edge 78 of a flap. The outer portions 88 are suitably bonded to the containment flaps 70 at an attachment point 90 that is spaced from the base 76 by from about 25 to about 95 percent of the flap height, and more particularly by from about 50 to about 75 percent of the flap height. Because the base 76 of each containment flap 70 is spaced from the absorbent assembly 42 by at least about 5 mm. and more particularly by at least about 8 mm. such as from about 10 to about 50 mm, fecal reservoirs 86 are formed transversely outward of the absorbent assembly 42 to contain fecal matter. The fecal passage layer 94, which may be formed of the same material as the fecal passage members 84 described in relation to FIG. 4, allows fecal matter to pass easily therethrough into the void volume of the fecal reservoirs 86.

The illustrated embodiment also includes an optional bodyside liner 44 disposed between the fecal passage layer 94 and the absorbent assembly 42. Alternatively, the fecal passage layer 94 may be disposed directly on the absorbent assembly 42 and function as a bodyside liner (not shown). The inner portion 87 of the fecal passage layer 94 may be bonded to the bodyside liner 44 by adhesives, thermal bonds, ultrasonic bonds, or other suitable means.

Figure 6:
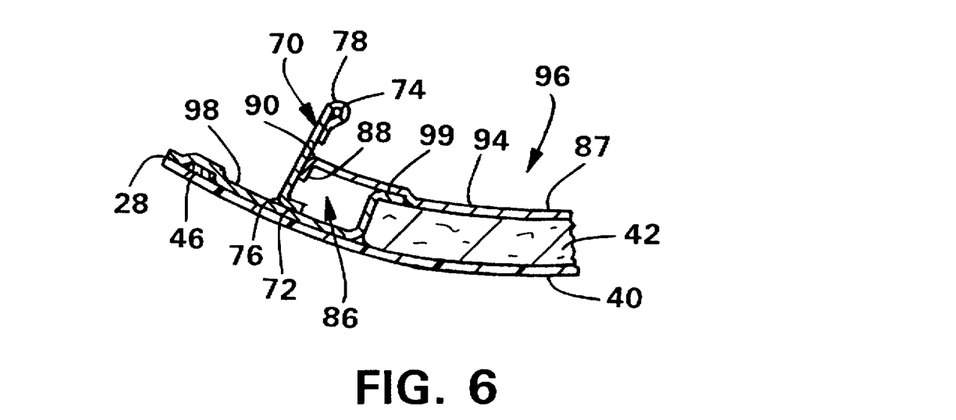
FIG. 6 representatively shows an enlarged transverse section view illustrating portions of a still further alternative absorbent article according to the present invention, in a relaxed condition.

The alternative embodiment illustrated by diaper 96 in FIG. 6 is similar to the diaper 92 of FIG. 5, except that a pair of leakage guards 98 (only one shown) are substituted for the bodyside liner 44. Each leakage guard 98, only one of which is shown, has an inner edge 99 positioned on top of the absorbent assembly 42. The inner edge 99 is disposed between the fecal passage layer 94 and the absorbent assembly 42 adjacent the periphery of the absorbent assembly. The leakage guards 98 are desirably formed of a liquid impermeable material and as a result tend to inhibit lateral movement of liquid.

TEST PROCEDURES
Wet Compression Recovery Test

This test has been designed to measure the compression recovery of a material when it is wet. The wet compression recovery indicates the ability of a material to recover to its original volume after being subjected to a compressing force. Wet compression recovery is determined from void volume measurements and is measured using an INSTRON or SINTECH tensile tester which measures the resisting force as a material is compressed between a movable platen and a fixed base at a constant rate using a certain amount of force and subsequently releasing the force at the same rate.

Suitable equipment for this test could include: Compression tester: INSTRON model 6021 with compression test software and 1kN load cell made by Instron of Bucks, England.
Balance: Mettler of Highstown, N. J., model PM4600

Preferably pressure, or force, and platen position are recorded. If only force is recorded, pressure is calculated using:

$$P = \frac{F}{A_p} \cdot 10{,}000 \text{ cm}^2/\text{m}^2$$

where:
P=pressure in Pascals
F=force pushing back on the platen in Newtons
$A_p$ =area of the platen in square centimeters (18.9 cm$^2$)
Void volume for a given material is calculated as follows:

$$VV = \frac{Vol}{M} - \frac{1}{P_{fiber}}$$

where:
VV=void volume of the material sample in cubic centimeters per gram
Vol=volume of the material sample in cubic centimeters
M=mass of the material sample in grams
$P_{fiber}$ =fiber density in grams per cubic centimeter
For materials made with multiple fiber types, the material fiber density is the weight average of each individual fiber density:

$$P_{fiber,\ Total} = wt\ \%_{fiber\ 1} \cdot P_{fiber\ 1} + wt\ \%_{fiber\ 2} \cdot P_{fiber\ 2} + \cdots$$

where:
wt % = weight percent of the fiber type in the material or $$wt\ \% = \frac{\text{fiber weight in composition}}{\text{total composition weight}} \times 100\%$$

When a foam material is being measured, $P_{fiber}$ is the density of the material from which the foam is fabricated. For example, if the foam material is a polyurethane foam, $P_{fiber}$ is the density of polyurethane. For foam materials, the void volume (VV) calculated using the preceding equation is an approximation and the actual void volume will become less than the calculated void volume (VV) as the number of closed cells within the foam material increases.

The void volume of a material will vary as the load upon the material varies. The void volume of the material for a given platen position is calculated using the void volume equation set forth above wherein:

$$Vol=(x_o-x) \cdot A_m \cdot 0.1 \text{cm/mm}$$

where:
Vol=volume of material in cubic centimeters
$X_o$=initial platen position from the base in millimeters
x=platen position from initial position in millimeters
$A_m$=area of sample material in square centimeters
The base must be larger in size than the platen. Zero height between platen and base distance was set by bringing the platen down until it barely touches the base. The platen was then raised to the desired initial height from the zero distance. The initial platen position must be greater than the initial thickness of the sample material so that the test starts out at zero pressure on the sample. The sample material can be the same size as the platen or larger.

For the purpose of measuring wet void volume for the present specification, a 4.9 cm diameter circular platen was used to compress materials against the base at a rate of 5.08 mm/min up to a 1.32 kg load (6,900 Pascal or 1.00 lb/in$^2$ pressure). The platen was then returned at the same rate to the initial starting position. The initial starting position for the platen was the sample material thickness plus 1 mm from the base. Material samples were cut to 50.4 mm diameter circles and were tested in the center. Force and position data were recorded at uniform periods of time between 0.05 and 0.01 minutes. The test is run on five material samples and the results averaged.

Wet void volume was measured when the material sample was completely immersed in 0.9% aqueous saline throughout the test. A flat bottomed container such as a hexagonal polystyrene weighing dish catalog #02-202D from Fischer Scientific of Pittsburgh, Pa. was placed on the base and the platen was zeroed and set to the initial position as described above. A 0.9% aqueous saline solution was added to the container to fill it to a level just to the bottom of the platen at its initial position. An appropriate saline could be S/P certified blood bank saline made by Stephens Scientific of Riverdale, N. J. and distributed by Baxter Healthcare of McGraw Park, Ill. under catalog #B3158-1. For the purpose of measuring void volume for the present specifications, 120 ml of saline was placed in the container and the platen was initially set a distance equal to 1 mm greater than the thickness of the test material sample from the base.

The load cell was tared with this level of fluid in the container. The sample was placed in the fluid, under the platen and the test was then performed as described above. Buoyant force was found to have a negligible effect on pressure but if so desired it can be subtracted from the pressure readings at each platen position using the following equation:

$$P_B = p_{saline} \cdot g \cdot (x_o - x) \cdot \left| \frac{A_p}{A_d - A_p} + 1 \right| \cdot 0.01$$

where:

$P_B$=Pressure from buoyant force in Pascals $P_{saline}$=saline (fluid) density in grams per cubic centimeter $A_p$=area of the platen in square centimeters (18.9 cm$^2$)

$A_d$=area of the dish in square centimeters $x_o$=initial platen position from the base in millimeters x=platen position in millimeters g=standard acceleration of gravity which is 981 cm/seconds$^2$ 0.01=conversion factor =0.1 cm/mm ·0.001 kg/gm ·100 cm/m The overall pressure on the sample becomes:

$P_{sample} = P_{reading} = P_B$ where:

$P_{sample}$=pressure on the sample from the platen in Pascal $P_{reading}$=pressure reading from the SINTECH or INSTRON in Pascal $P_B$=buoyancy pressure from the 0.9% saline in Pascal Wet compression recovery was calculated using the platen positions on initial compression to 68.9 Pascal and on recovery when the pressure was equal to 68.9 Pascal:

$$\% \text{ Wet Compression Recovery} = \frac{VV_{recovery\ 68.9\ Pa}}{VV_{compress\ 68.9\ Pa}} \times 100$$

where:

$VV_{recovery}$ 68.9 Pa=void volume upon recovery at 68.9 Pascal pressure $VV_{compress}$ 68.9 Pa=void volume upon initial compression to 68.9 Pascal pressure Pore Size Test This test has been designed to measure the mean pore size of a sample of material which may be used in an absorbent article, such as an infant diaper. The sample of material has a thickness of about 0.25 inches (0.64 centimeters), a width of about 2.0 inches (5.1 centimeters), and a length of about 2.5 inches (6.35 centimeters). The sample is placed on a glass microslide having a width of 2.0 inches (5.1 centimeters) and a length of 3.0 inches (7.62 centimeters). The surface of the sample is coated with a 2:1 diluted solution of Pentel®Correction Fluid and isopropyl alcohol. The Pentel®Correction Fluid is commercially available from Pentel Co., Ltd., a business having offices located in Japan. The diluted solution migrates through the sample and is allowed to dry. The drying solution cements the sample to the glass microslide.

The microslide having the dried, coated sample adhered thereon is placed on a macroviewer stand and viewed through a 50 MM El-Nikkor f/2.8 enlarging lens. Lighting is provided by an 8-bulb octagonal ring illuminator that surrounds the lens to provide "incident darkfield" conditions. The mean pore size of the sample of material is determined using a Quantimet 970 Image Analyzer which is commercially available from Leica Instruments, Inc., a business having offices located in Deerfield, Ill. Major cut polygons and minor window faces are selected manually with a "light pen" when they are approximately orthogonal to the viewing plane. A program was developed to analyze the individual measurements and organize them into a histogram showing the total number of pores, the mean pore size and the standard deviation of the pore size.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. Therefore, the invention should not be limited by the specific embodiments described, but only by the claims.

We claim:

1. An absorbent article having longitudinal and transverse axes, longitudinal end edges, and longitudinal side edges extending between the longitudinal end edges, the absorbent article comprising:

a moisture barrier;

an absorbent assembly disposed on the moisture barrier; and fecal containment members positioned transversely outward of the absorbent assembly between the absorbent assembly and each longitudinal side edge, the fecal containment members having a wet compression recovery of at least about 85 percent and a mean pore size of at least about 1.5 millimeters.

2. The absorbent article of claim 1, wherein the fecal containment members have a height dimension that is greater than a height dimension of the absorbent assembly.

3. The absorbent article of claim 1, further comprising a bodyside liner bonded to the moisture barrier and sandwiching the absorbent assembly therebetween, the bodyside liner disposed between the fecal containment members and the moisture barrier.

4. The absorbent article of claim 1, further comprising a bodyside liner bonded to the moisture barrier and sandwiching the absorbent assembly therebetween, the fecal containment members disposed between the bodyside liner and the moisture barrier.

5. The absorbent article of claim 4, wherein portions of the bodyside liner disposed on the fecal containment members have a pore structure adapted to permit passage of fluidic fecal matter.

6. The absorbent article of claim 1, wherein the fecal containment members each have a transverse cross-sectional area of at least about 2.5 square centimeters.

7. The absorbent article of claim 6, wherein the fecal containment members each have a transverse cross-sectional area of from about 7.5 to about 12.5 square centimeters.

8. The absorbent article of claim 1, wherein the fecal containment members each have a width dimension of from about 15 to about 25 millimeters.

9. The absorbent article of claim 1, further comprising containment flaps disposed on the moisture barrier transversely outward of the fecal containment members.

10. The absorbent article of claim 1, wherein the fecal containment members have a wet compression recovery of from about 90 to about 100 percent.

11. The absorbent article of claim 1, wherein the fecal containment members have a void volume of at least about 20 cubic centimeters per gram when under no load.

12. The absorbent article of claim 1, wherein the fecal containment members comprise a polyurethane foam material.

13. The absorbent article of claim 1, wherein the fecal containment members are substantially hydrophobic.

14. The absorbent article of claim 1, wherein the fecal containment members have a mean pore size of from about 2 to about 4 millimeters.

15. The absorbent article of claim 1, wherein the fecal containment members are capable of maintaining at least about 25 percent of their void volume when under a load of 0.673 Newtons per square centimeter.

16. The absorbent article of claim 1, wherein the fecal containment members are spaced from one another by at least about 5 centimeters.

17. An absorbent article having longitudinal and transverse axes, longitudinal end edges, and longitudinal side edges extending between the longitudinal end edges, the absorbent article comprising:

a moisture barrier;

an absorbent assembly disposed on the moisture barrier; and fecal containment members positioned transversely outward of the absorbent assembly between the absorbent assembly and each longitudinal side edge, the fecal containment members having a wet compression recovery of at least about 85 percent, a void volume of at least about 20 cubic centimeters per gram when under no load, and a mean pore size of from about 2 to about 4 millimeters.

18. The absorbent article of claim 17, wherein the fecal containment members are capable of maintaining at least about 25 percent of their void volume when under a load of 0.673 Newtons per square centimeter.

19. The absorbent article of claim 17, wherein the fecal containment members are substantially free of high-absorbency material.

20. The absorbent article of claim 19, wherein the fecal containment members are substantially hydrophobic.

21. The absorbent article of claim 17, wherein the fecal containment members each have a transverse cross-sectional area of at least about 2.5 square centimeters.

22. The absorbent article of claim 21, wherein the fecal containment members have a height dimension that is greater than a height dimension of the absorbent assembly.

23. The absorbent article of claim 17, further comprising a bodyside liner bonded to the moisture barrier with the fecal containment members disposed between the bodyside liner and the moisture barrier, portions of the bodyside liner disposed on the fecal containment members having a pore structure adapted to permit passage of fluidic fecal matter.

24. The absorbent article of claim 17, further comprising containment flaps disposed on the moisture barrier transversely outward of the fecal containment members.

25. An absorbent article having longitudinal and transverse axes, longitudinal end edges, and longitudinal side edges extending between the longitudinal end edges, the absorbent article comprising:

a moisture barrier;

an absorbent assembly disposed on the moisture barrier; and fecal containment members positioned transversely outward of the absorbent assembly between the absorbent assembly and each longitudinal side edge, the fecal containment members having a wet compression recovery of from about 90 to about 100 percent, a void volume of from about 30 to about 50 cubic centimeters per gram when under no compressive load, and a mean pore size of from about 2 to about 4 millimeters, each fecal containment member having a transverse cross-sectional area of at least about 2.5 square centimeters and being substantially free of high-absorbency material.

26. The absorbent article of claim 25, where in the fecal containment members are capable of maintaining at least about 25 percent of their void volume when under a load of 0.673 Newtons per square centimeter.

27. The absorbent article of claim 25, wherein the fecal containment members are substantially hydrophobic.

28. The absorbent article of claim 25, wherein the fecal containment members each have a transverse cross-sectional area of from about 7.5 to about 12.5 square centimeters.

29. The absorbent article of claim 25, wherein the fecal containment members have a height dimension that is greater than a height dimension of the absorbent assembly.

30. The absorbent article of claim 25, wherein the fecal containment members each have a width dimension of from about 15 to about 25 millimeters.

31. The absorbent article of claim 25, further comprising containment flaps disposed on the moisture barrier transversely outward of the fecal containment members.

32. The absorbent article of claim 25, wherein the fecal containment members comprise a foam material having a density of from about 0.010 to about 0.030 grams per cubic centimeter.

* * * * *